United States Patent

Curran

[11] 3,976,773
[45] Aug. 24, 1976

[54] PIPERAZINE DIONES
[75] Inventor: Adrian Charles Ward Curran, Newcastle-upon-Tyne, England
[73] Assignee: John Wyeth & Brother Limited, Maidenhead, England
[22] Filed: Mar. 14, 1975
[21] Appl. No.: 558,575

[30] Foreign Application Priority Data
Mar. 19, 1974 United Kingdom............... 12051/74

[52] U.S. Cl............................ 424/250; 260/268 DK
[51] Int. Cl.²...................................... C07D 295/00
[58] Field of Search................ 260/268DK; 424/250

Primary Examiner—Nicholas S. Rizzo
Assistant Examiner—Jose Tovar

[57] ABSTRACT

This invention relates to piperazine diones having the formula:

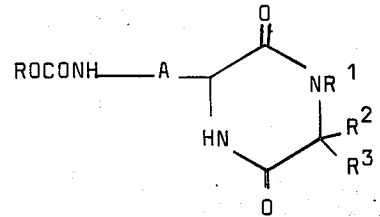

wherein R represents a phenyl lower alkyl radical in which the phenyl portion may be substituted by halogen, lower alkyl or lower alkoxy; A represents a straight or branched chain lower alkylene radical; $R^1$ represents hydrogen or lower alkyl; and $R^2$ and $R^3$ independently represent hydrogen or alkyl of 1 to 3 carbon atoms, which possess anti-ulcer activity.

8 Claims, No Drawings

PIPERAZINE DIONES

This invention relates to novel piperazine dione derivatives possessing pharmacological activity, to processes for preparing them and to pharmaceutical compositions containing them.

More particularly this invention relates to novel piperazine diones having the formula:

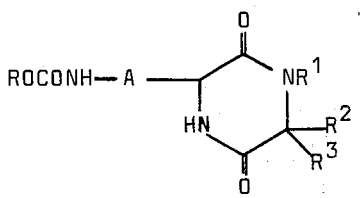

(I)

wherein R represents a phenyl lower alkyl radical, in which the phenyl portion may be substituted by halogen, lower alkyl or lower alkoxy; A represents a straight or branched chain lower alkylene group; $R^1$ represents hydrogen or lower alkyl; and $R^2$ and $R^3$ independently represent hydrogen or alkyl of 1 to 3 carbon atoms.

By the term "lower" used in connection with the groups alkyl, alkylene or alkoxy is meant an alkyl, alkylene or alkoxy group which contains from 1 to 6 carbon atoms and includes both straight and branched chains.

Examples of the phenyl portion of R when substituted phenyl are phenyl substituted by one or more groups which may be the same or different selected from fluorine, chlorine, bromine, methyl, ethyl, propyl, butyl, methoxy, ethoxy, propoxy and butoxy. Groups represented by R include benzyl, phenethyl, 3-phenylpropyl, all of which may be optionally substituted by one or more of the same groups mentioned above for the phenyl portion. Preferably R is benzyl or benzyl substituted by halogen, for example p-chlorobenzyl, o-chlorobenzyl. Examples of straight chain A radicals are methylene, ethylene, propylene and butylene; examples of branched chain A radicals are

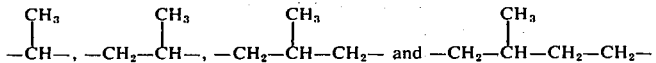

Preferably A is a straight chain of 1 to 4 carbon atoms.

Examples of $R^1$ are hydrogen, methyl, ethyl, n-propyl, isopropyl and n-butyl. Examples of $R^2$ and $R^3$ are hydrogen, methyl, ethyl and n-propyl. Preferably, $R^1$, $R^2$ and $R^3$ all represent hydrogen.

It will be apparent to anyone skilled in the art that the compounds of formula (I) possess at least one asymmetric carbon atom and therefore optical isomers are possible. All such optical isomers or mixtures thereof are intended to be included within the scope of the present invention.

The compounds of formula (I) possess pharmacological activity, in particular, anti-ulcer activity. The anti-ulcer activity of the compounds of formula (I) is determined by a method based on that of Brodie and Hanson, J. App. Physiol. 15:291 (1960). The test procedure was:

Male rats, weighing between 80 and 120 gms., are fasted overnight with water ad lib. The rats are then divided into groups of six and dosed orally with the test drug, or with the vehicle alone, 0.5% carboxymethylcellulose, in volume of 10 ml/kg. After 30 minutes the rats are inserted into aluminium restraining tubes measuring 1⅝ inches in diameter by 5 inches and placed in the cold (4′±1°C) for 3 hours. Immediately after cold exposure the rats are killed by intracranial alcohol injection and their stomachs excised and opened along the greater curvature. Each stomach is gently rinsed free of contents with warm tap water and pinned out on a board. The condition of the gastric mucosa is then scored from 0 to 6 on the following scale:

| Ulcers 0 to 6 | |
|---|---|
| 0 | = No ulcers |
| 1 | = Pin-point haemorrhagic site |
| 2, 3 | = Several discrete pin-point haemorrhagic sites |
| 4, 5, 6 | = Large eroded sites with haemorrhage |

The maximum possible score for each animal is 6 and for the group 36. Decrease in ulcer formation is calculated as a percentage of the control score, i.e.

$$\text{Percentage inhibition} = \frac{\text{Total control group score} - \text{Total test group score}}{\text{Total control group score}} \times 100$$

The statistical significance of the effect is assessed by Student's t-test.

In the above test a representative compound of formula I, namely 3-(-4-benzyloxycarbonylaminobutyl)-2,5-piperazinedione showed good activity.

The present invention also includes processes for preparing the compounds of formula (I). One such process for preparing compounds of formula (I) comprises cyclising a compound of formula:

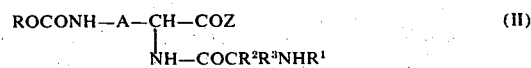

(II)

wherein R, $R^1$, $R^2$, $R^3$ and A are as defined above and Z is hydroxy, or halogen, e.g. chlorine or bromine or —COZ is an ester function, for example a lower alkyl ester, e.g. methyl ester; an amido function or a thioester function for example a thioaryl ester, e.g. thiophenyl ester. When —COZ is an ester or amide function the reaction may be effected by allowing the compound of formula (II) to stand in solution, for example, in alcohol; alcoholic ammonia, e.g. methanolic ammonia; or aqueous solution, for a period of time sufficient to permit cyclisation to occur. When Z is hydroxy the cyclisation reaction may be accelerated or brought to completion by the action of heat. When Z is halogen the cyclisation reaction may be carried out in the presence of base, for example an alkali metal hydroxide, e.g. NaOH.

Some of the compounds of formula (II) are known compounds and reference may be made to the literature for methods of preparing them. The novel compounds of formula (II) may be prepared by analogous processes. For example compounds of formula (II) wherein A is butylene, Z is hydroxy and $R^1$, $R^2$ and $R^3$ are hydrogen, may be prepared by reacting an $N^\epsilon$ — substituted — lysine derivative of formula:

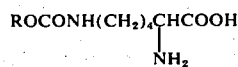    (III)

wherein R is as defined above with an α-haloacetic acid halide to give a compound of formula:

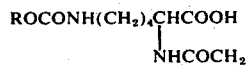    (IV)

and then reacting the compound of formula (IV) with aqueous ammonia. Compounds of formula (II) wherein A, $R^1$, $R^2$ and $R^3$ have meanings other than those described immediately above may be prepared using the appropriate starting materials.

Another process for preparing the compounds of formula (I) wherein $R^1$ is hydrogen comprises reacting a compound of formula:

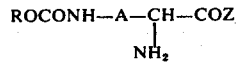    (V)

wherein R and A are as defined above and —COZ is an ester function, with a compound of formula:

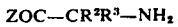    (VI)

wherein —COZ is an ester function and $R^2$ and $R^3$ are as defined above. The reaction is usually accelerated or brought to completion by the action of heat. Preferably —COZ is a lower alkyl ester function, most preferably the methyl ester.

Yet another process for preparing the compounds of formula (I) comprises reacting a compound of formula:

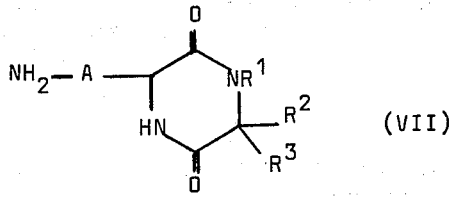    (VII)

wherein $R^1$, $R^2$, $R^3$ and A are as defined above, with a compound of formula

ROOC—X    (VIII)

wherein R is as defined above and X is a halogen, e.g. chlorine. The reaction may conveniently be carried out in the presence of base, for example an alkali metal hydroxide or bicarbonate.

The compounds of formula (VII) may be prepared from the corresponding compounds of formula:

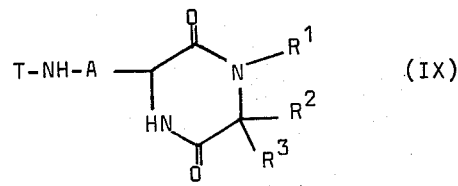    (IX)

wherein T is a protecting group known in the art for protecting an amino function, by mild hydrolysis, hydrogenolysis or some other reaction known in the art for removing the group T. The compounds of formula (IX) may themselves be prepared following the information already given using an appropriate starting material containing the group T. Examples of the group T are p-toluenesulphonyl, trityl and benzyloxycarbonyl.

With regard to other groups suitable for protecting the amino function reference may be made to the literature, e.g. Chemistry of the Amino Acids by Greenstein and Winitz, Volume 2, pages 885–924 (John Wiley & Sons. Inc. 1961).

The invention also includes pharmaceutical composition comprising a compound of formula I and a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical compositions is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate magnesium trisilicate, sodium bicarbonate or the alumina gel described in U.K. Pat. No. 1,284,394.

The following Examples illustrate the invention; Example 1 concerns the preparation of a starting material; Examples 2 to 10 concern novel compounds of this invention:

EXAMPLE 1

$N^\alpha$-glycyl-$N^\epsilon$-carbobenzoxy-L-lysine methyl ester $N^\alpha$-Glycyl-$N^\epsilon$-carbobenzoxy-L-lysine (10.1 g.) prepared by the method of Rao et al. (*J. Biol. Chem.*, 198,507 1952) was dissolved in methanol (150 ml.) and treated with boron trifluoride etherate (30 ml.) and the mixture heated at 80°C for 25 hours. The solvent was removed in vacuo and the residual oil dissolved in water (100 ml.) and extracted with ether (2 × 50 ml.) and the extracts discarded. The aqueous solution was adjusted to pH 9.0 with 4N sodium hydroxide, saturated with sodium chloride and extracted with ethyl acetate (3 × 50 ml.). The combined extracts were washed with saturated brine, dried (MgSO₄) and the solvent removed in vacuo to give a residual oil which was redissolved in ethanol (10 ml.) and treated with an excess of an ethereal solution of hydrogen chloride. The solid was filtered and recrystallised from isopropanol/diisopropyl ether to give $N^\alpha$-glycyl-$N^\epsilon$-carbobenzoxy-L-lysine methyl ester hydrochloride, needles (4.5 g.) m.p. 122°C. (Found: C, 53.0; H, 6.8; N, 10.8. $C_{17}H_{25}N_3O_5$. HCl requires: C, 52.6; H, 6.7; N, 10.8%).

EXAMPLE 2

3-(4-Benzyloxycarbonylaminobutyl)-2,5-piperazinedione

The $N^\alpha$-glycyl-$N^\epsilon$-carbobenzoxy-L-lysine methyl ester prepared as described in Example 1 was dissolved in methanol previously saturated with ammonia (300 ml.) and allowed to stand for 3 days in a sealed flask at ambient temperature. The solvent was removed in vacuo and the residual solid recrystallised from absolute ethanol to give the title compound as colourless needles (1 g.) m.p. 210°C. (Found: C, 59.9; H, 6.7; N, 13.5. $C_{16}H_{21}N_3O_4$ requires: C, 60.1; H, 6.5; N, 13.2%).

EXAMPLE 3

3-(3-p-Chlorobenzyloxycarbonylaminopropyl)-2,5-piperazinedione

Using an analogous precedure to Example 2 methyl 2-(N-glycylamino)-5-(N-p-chlorobenzyloxycarbonylamino) pentanoate may be cyclised to give the title compound.

EXAMPLE 4

3-(2-p-Chlorobenzyloxycarbonylaminoethyl)-2,5-piperazinedione

Using analogous procedure to Example 2, methyl 2-(N-glycylamino)-4-(N-p-chlorobenzyloxycarbonylamino) butanoate may be cyclysed to give the title compound.

EXAMPLE 5

3-(p-Chlorobenzyloxycarbonylaminomethyl)-2,5-piperazinedione

Using an analogous procedure to Example 2, methyl 2-(N-glycylamino)-3-(N-p-chlorobenzyloxycarbonylamino) propanoate may be cyclised to give the title compound.

EXAMPLE 6

3-(4-p-Methylbenzyloxycarbonylaminobutyl)-2,5-piperazinedione

Using an analogous procedure to Example 2, $N^\alpha$-glycyl-$N^\epsilon$-p-methylbenzyloxycarbonyl-L-lysine methyl ester may be cyclised to give the title compound.

EXAMPLE 7

3-(4-p-Methoxybenzyloxycarbonylaminobutyl)-2,5-piperazinedione

Using an analogous procedure to Example 2, $N^\alpha$-glycyl-N+-p-methoxybenzyloxycarbonyl-L-lysine methyl ester may be cyclised to give the title compound.

EXAMPLE 8

3-(4-p-Fluorobenzyloxycarbonylaminobutyl)-2,5-piperazinedione

Using an analogous procedure to Example 2, N - glycyl-N -p-fluorobenzyloxycarbonyl-L-lysine methyl ester may be cyclised to give the title compound.

EXAMPLE 9

3-(4-Benzyloxycarbonylaminobutyl)-1-methyl-2,5-piperazinedione

Using an analogous procedure to Example 2, N - (N-methylglycyl)-N -carbobenzoxy-L-lysine methyl ester may be cyclised to give the title compound.

EXAMPLE 10

3-(4-Benzyloxycarbonylaminobutyl)-6,6-dimethyl-2,5-piperazinedione

Using an analogous procedure to Example 2, N - (2,2-dimethylglycyl)-N -carbobenzoxy-L-lysine methyl ester may be cyclised to give the title compound.

I claim:
1. A compound having the formula:

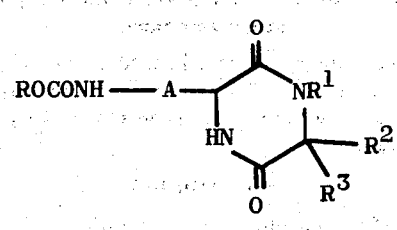

wherein R represents a benzyl, phenethyl, or 3-phenyl propyl group in which the phenyl portion may be mono-substituted by fluorine, chlorine, bromine, methyl, ethyl, propyl, butyl, methoxy, ethoxy, propoxy, or butoxy; A represents a methylene, ethylene, propylene, or butylene group; $R^1$ represents hydrogen, methyl, ethyl, n-propyl, isopropyl or n-butyl; and $R^2$ and $R^3$ independently represent hydrogen, methyl, ethyl, or n-propyl.

2. A compound as claimed in claim 1, wherein R is benzyl.

3. A compound as claimed in claim 1 wherein $R^1$ represents hydrogen or methyl.

4. A compound as claimed in claim 1 wherein $R^2$ and $R^3$ independently represent hydrogen or methyl.

5. A compound as claimed in claim 1 which is 3-(4-benzyloxycarbonylaminobutyl)-2,5-piperazinedione.

6. A pharmaceutical composition for the treatment of gastric ulcers consisting essentially of effective amount of a compound as claimed in claim 1 together with a pharmaceutically acceptable carrier and an antacid ingredient.

7. The anti-ulcer composition of claim 6 wherein the compound is 3-(4-benzyloxycarbonylaminobutyl)-2,5-piperazinedione.

8. A method of treating gastric ulcers in an effected host which comprises administering to said host an effective amount of a compound having the formula:

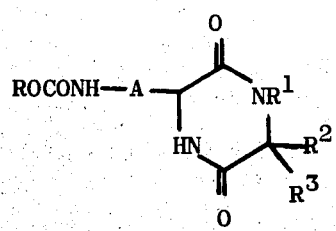

wherein R represents a benzyl, phenethyl, or 3-phenyl propyl group in which the phenyl portion may be mono-substituted by fluorine, chlorine, bromine, methyl, ethyl, propyl, butyl, methoxy, ethoxy, propoxy, or butoxy; A represents a methylene, ethylene, propylene, or butylene group; $R^1$ represents hydrogen, methyl, ethyl, n-propyl, isopropyl, or n-butyl; and $R^2$ and $R^3$ independently represent hydrogen, methyl, ethyl, or n-propyl.

* * * * *